(12) United States Patent
Yu et al.

(10) Patent No.: US 7,977,074 B2
(45) Date of Patent: Jul. 12, 2011

(54) METHOD OF BIOSYNTHESIZING TETRODOTOXIN

(75) Inventors: Peter Hoi-fu Yu, Kowloon (HK); Chun Fai Yu, Kowloon (HK)

(73) Assignee: The Hong Kong Polytechnic University, Hong Kong (HK)

( * ) Notice: Subject to any disclaimer, the term of this patent is extended or adjusted under 35 U.S.C. 154(b) by 545 days.

(21) Appl. No.: 11/709,657

(22) Filed: Feb. 23, 2007

(65) Prior Publication Data

US 2008/0206825 A1    Aug. 28, 2008

(51) Int. Cl.
*C12P 17/18*    (2006.01)
(52) U.S. Cl. ........................................ 435/119
(58) Field of Classification Search ............... None
See application file for complete search history.

(56) References Cited

OTHER PUBLICATIONS

Simidu et al., International Journal of Systematic Bacteriology, 1990, vol. 40, No. 4 , p. 331-336.*
Yu et al., Toxicon 44, Nov. 2004, p. 641-647.*
Estrada-Badillo et al., World Journal of Microbiology and Biotechnology, 2003, vol. 9, p. 129-133.*
Thompson et al., Microbiology and Molecular Biology Reviews, 2004, vol. 68, No. 3 p. 403-431.*
Wu et al., Toxicon, 2005, vol. 45, p. 851-859.*
Chen et al., Acta Zoologica Taiwanica, 1998, vol. 9. No. 1, p. 41-48.*
Yu et al./ Two novel species of tetrodotoxin-producing bateria isolated from toxic marine puffer fished/ Toxicon44 (2004) 641-647.
Okada et al./ Vibrios Commonly Possess Two Chromosomes/Journal of Bacteriology/ Jan. 2005/ p. 752-757.
Audris Huang/ Synthetic Approaches to Tetrodotoxin 2007.

* cited by examiner

*Primary Examiner* — Kade Ariani
(74) *Attorney, Agent, or Firm* — Frommer Lawrence & Haug LLP; Ronald R. Santucci

(57) ABSTRACT

The present invention relates methods for the biosynthesis of tetrodotoxin (TTX) involving the steps of obtaining a culture possessing one or more of a *Vibrio* species, such as through a seed culture, inoculating the culture and tissue extract from a textrodotoxin-bearing organism in a fermenter medium, and isolating and purifying tetrodotoxin from said fermenter, resulting in a yield of TTX of about 0.5 g TTX/L in about 3 to 5 days, such TTX being at least 90% pure.

12 Claims, 3 Drawing Sheets

```
┌─────────────────────┐
│  OBTAINING VIBRIO   │─── 101
│      CULTURE        │
└─────────────────────┘
          │
          ▼
┌─────────────────────┐
│ INOCULATING VIBRIO  │
│    CULTURE and      │─── 103
│  TISSUE EXTRACT IN  │
│      FERMENTER      │
└─────────────────────┘
          │
          ▼
┌─────────────────────┐
│      ISOLATING      │
│    TETRODOTOXIN     │─── 105
│  FROM CULTURE MEDIUM│
└─────────────────────┘
          │
          ▼
┌─────────────────────┐
│      PURIFYING      │─── 107
│    TETRODOTOXIN     │
└─────────────────────┘
```

FIG. 1

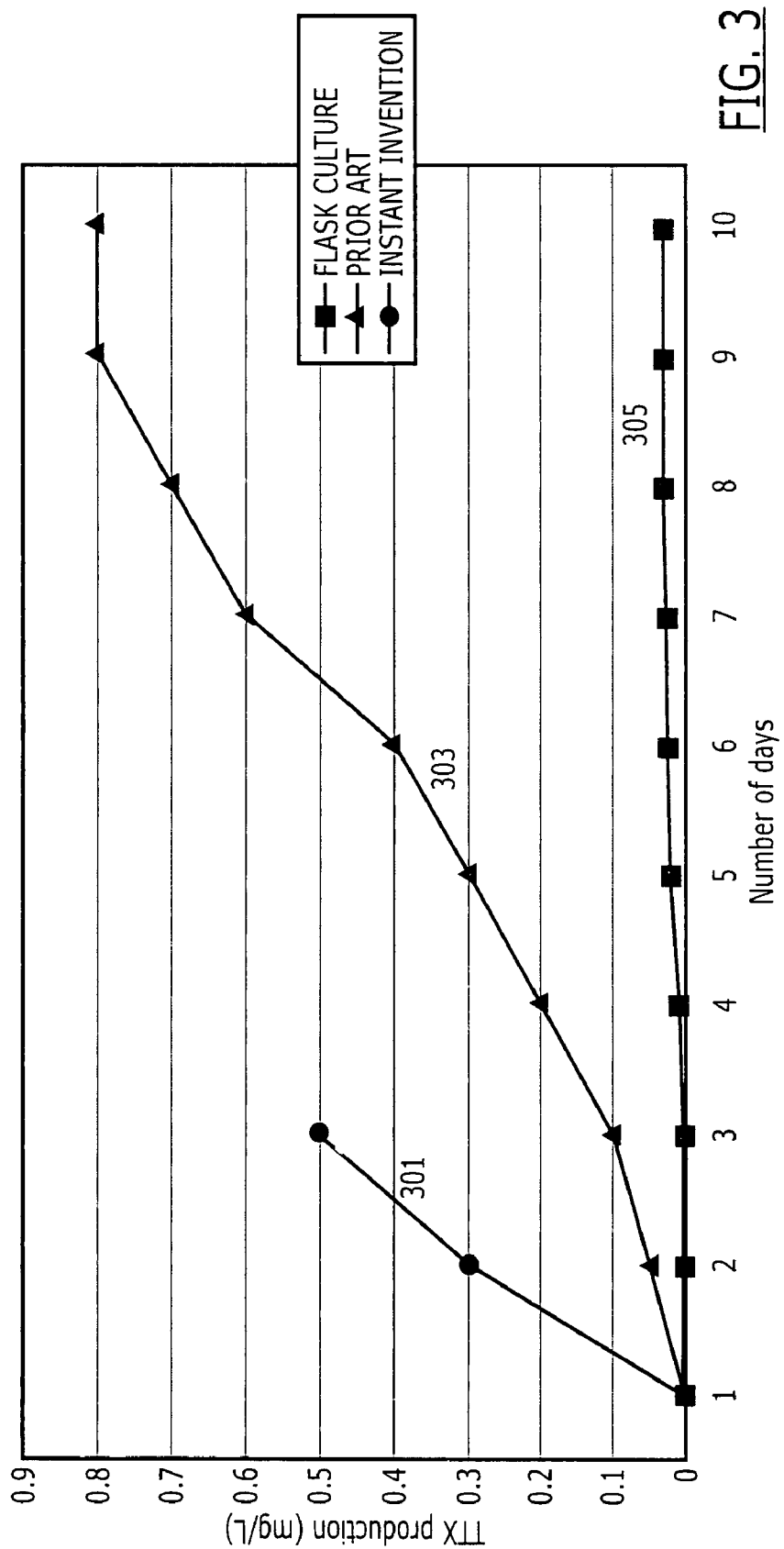

US 7,977,074 B2

METHOD OF BIOSYNTHESIZING TETRODOTOXIN

BACKGROUND

Tetrodotoxin (TTX) was first isolated from the ovaries of the puffer fish. Since then, it has been commercially extracted and purified for many years. However, the extraction rate of TTX is extremely low, about 1 g TTX per 100 Kg of ovaries, thus making it one of the highest priced natural neurotoxins. Further, the industry is subject to slow down as stocks of puffer fish have been falling due to over production.

In light of these negatives, many researchers continue to propose new synthesis methodologies. The synthesis of tetrodotoxin presents a significant challenge to the organic chemist (Huang, "Synthetic Approaches to Tetrodotoxin"). For example, some methods include stereoselective methods used to incorporate the guanidine nitrogen at C8a position. Other approaches focus on novel rearrangements. But because of the continued complexity, it is still more economical to extract tetrodotoxin directly from puffer fish ovaries.

The drive to find more economical routes for TTX production is because of its potential as a novel pharmaceutical drug, being possibly useful in aiding cancer patients and potential use as a withdrawal formulation for heroin addicts. It is estimated that 1200 g of TTX will be required by 2 million cancer patients in a one-month treatment course, whilst 400 g of TTX will be required by another 2 million drug addicts every 10 days.

It is an object of the present system to overcome the disadvantages and problems in the prior art.

DESCRIPTION

The present invention proposes methods for the biosynthesis of tetrodotoxin (TTX) resulting in high yield, highly pure TTX.

The present invention also proposes methods for the isolation and purification of TTX.

These and other features, aspects, and advantages of the apparatus and methods of the present invention will become better understood from the following description, appended claims, and accompanying drawings where:

FIG. 1 shows a method of biosynthesizing TTX in accordance with the present invention.

Figure 2:
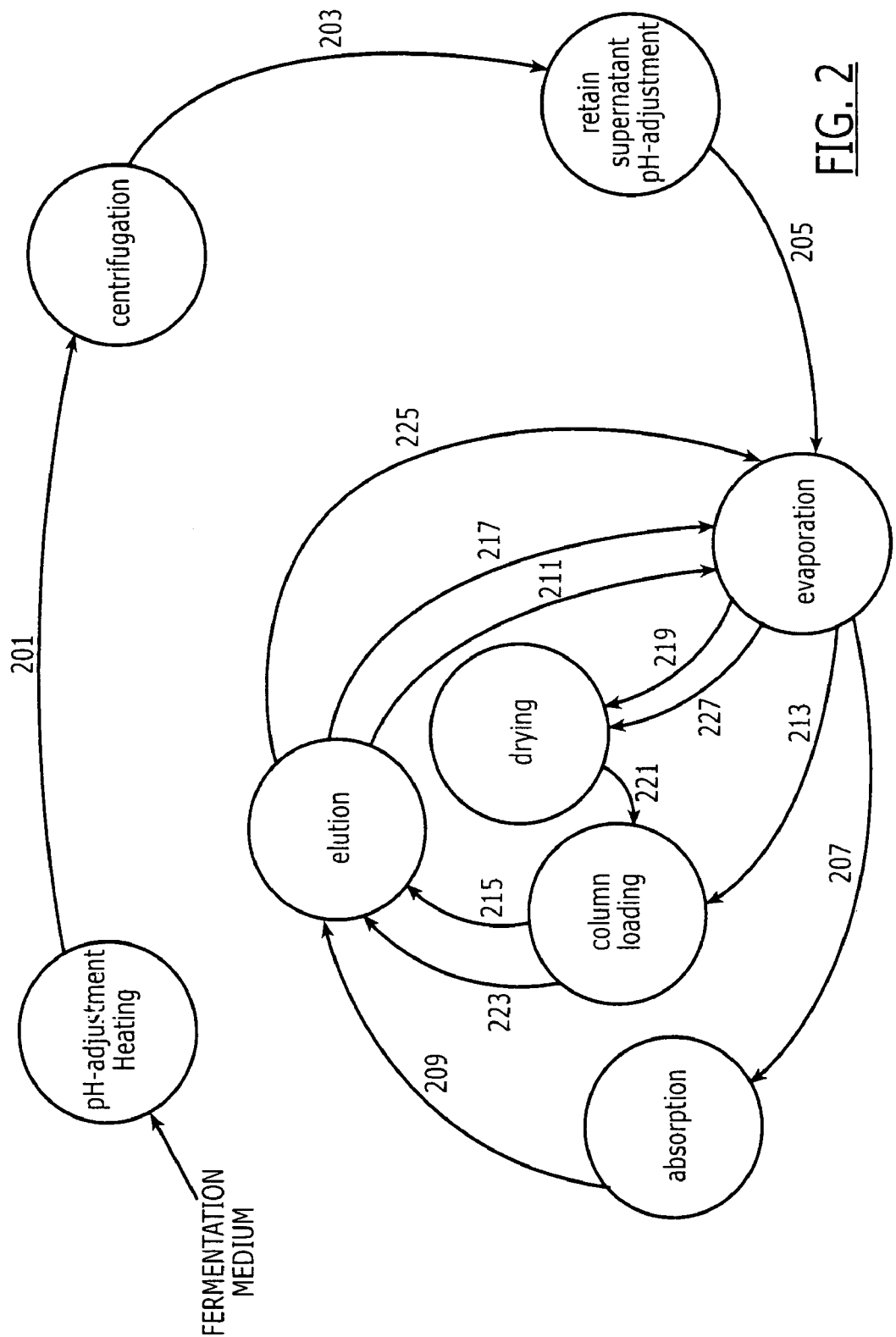
FIG. 2 shows a method of isolating and purifying TTX in accordance with the present invention.

FIG. 3 compares the results of the present invention's method of biosynthesizing TTX with results derived from prior art methods of TTX biosynthesis.

The following description of certain exemplary embodiment(s) is merely exemplary in nature and is in no way intended to limit the invention, its application, or uses. Throughout this description, "tetrodotoxin-bearing organism" shall refer to an organism that possesses the compound known as tetrodotoxin, chemical formula $C_{11}H_{17}O_8N_3$, and its analogues, including but limited to anhydrotetrodotoxin, tetrodaminotoxin, methoxytetrodotoxin, ethoxytetrodotoxin, deoxytetrodotoxin, and tetrodonic acid, in their organs either through endogenous means such as self-production, exogenous means such as the food chain, symbiotic relationship, or a combination of such. "Growth factors" shall refer to substances such as proteins that are present in an organisms tissues that allow stabilization of tetrodotoxin structure in the organisms tissues, such that the structure does not decompose or under an analogue modification.

Now, to FIGS. 1-3,

FIG. 1 is an embodiment for a method of biosynthesizing tetrodotoxin in accordance with the present invention, containing the steps of obtaining a culture possessing one or more *Vibrio* species 101, inoculating the *Vibrio* culture and a tissue extract in a fermenter 103, isolating the resultant tetrodotoxin from the culture medium 105, and purifying the tetrodotoxin 107.

Obtaining a culture possessing one or more *Vibrio* species 101 consists of gathering a culture upon which *Vibrio* species were grown. Gathering can include obtaining a properly stored culture, or a culture obtained from a seed culture. One or more *Vibrio* species in the culture can be selected from the group consisting of *Vibrio nigripulchritudo*, *Vibrio mediterranei*, *Vibrio harveyi*, *Vibrio alginolyticus*, *Vibrio salmonicida*, *Vibrio tubiashii*, *Vibrio parahaemolyticus*, *Vibrio campbellii*, *Vibrio natriegens*, *Vibrio nereis*, *Vibrio carchariae*, *Vibrio fluvialis*, *Vibrio fischeri*, *Vibrio vulnificus*, *Vibrio splendidus*, *Vibrio orientalis*, *Vibrio aestuarianus Vibrio pelagius*, *Vibrio wodanis*, *Vibrio furnissii*, *Vibrio proteolyticus*, *Vibrio ichthyoenteri*, *Vibrio pectenicida*, *Vibrio logei*, *Vibrio mimicus*, *Vibrio mytili*, *Vibrio rumoiensis*, *Vibrio anguillarum*, *Vibrio gazogenes*, *Vibrio halioticoli*, *Vibrio hollisae*, *Vibrio ordalii*, and *Vibrio metschnkiovii* and *Vibrio choleme*.

In a preferred embodiment, the *Vibrio* species are one or more of *Vibrio alginolyticus*, *Vibrio anguillarum*, *Vibrio choleme*, *Vibrio parahaemolyticus*, and *Vibrio fluvialis*.

*Vibrio* species samples for culturing can be obtained from the organs of tetrodotoxin-bearing organisms including flatworms, ribbon worms, gastropods, blue-ringed octopuses, starfish, sea urchins, xanthid crabs, horsehoe crabs, gobies, frogs, newts, and puffer fish. In one embodiment, the *Vibrio* species are obtained from puffer fish of the Tetraodontidae, Diodontidae, and Triodontidae families, for example *Arothron hispidis*, *Arothron stellatus*, *Chelonodon patocoa*, *Takifugu alboplumbeus*, *Takifugu niphobles*, *Takifugu oblongus*, *Takifugu ocellatus*, *Takifugu xanthopterus*, and *Diodon holocanthus*. In one embodiment, *Vibrio* species are obtained from *Chelonodon patoca*, *Takifugu alboplumbeus*, and *Takifugu niphobles*, specifically the species *Vibrio alginolyticus*. The organs, i.e. tissue, used to provide the *Vibrio* species can be the intestine, liver, ovary, stomach, and skin, used separately or in conjunction with one another. In one embodiment, *Vibrio* species are obtained from the ovary of *Takifugu niphobles*, the skin of *Chelonodon patoca*, and/or the intestine of *Takifugu alboplumbeus*.

In obtaining the *Vibrio* species from the organism tissues, the tissues are firstly exised, preferably aseptically, from the organism. The exised tissue is added to a bioreactor containing a culture medium, for example a shake flask, aeration-agitation bioreactor, percolated impellor bioreactor, draught tube air-lift bioreactor, draft tube with lasplan Turbine bioreactor, air-lift loop bioreactor, rotating drum bioreactor, and spin filter bioreactor. In one embodiment, a shake flask is used as the bioreactor. The bioreactor can be sized from about 250 ml to about 1 Liter. The bioreactor should contain a medium such as sterile seawater, seawater, based media and serum-free medium. In one embodiment, the bioreactor contains sterile seawater prior to the addition of the tissue (batch processing). The tissue in medium can be agitated between about 75 rpm to about 250 rpm for approximately 5 to 25 minutes.

Following agitations, from about 50 ml to 500 ml of the bioreactor contents are extracted into a second bioreactor containing a volume of medium, such volume ranging from about 25 ml to about 100 ml, the medium being either the same as in the first bioreactor, or different. In one embodiment, the medium in the second bioreactor is the same as that used in the first reactor. The final concentration in the second bioreactor should be from about 0.04 g tissue/ml to about 0.10 g tissue/ml.

An extract of about 10% of the previous second bioreactor volume is then taken out and placed onto a suitable substrate. The volume of extract can range from about 2.5 ml to about 60 ml. The substrate can be made of glass, plastic, ceramic, or a synthetic resin, and contain a growth medium, for example agar. The substrate can include adherent reactors such as roller bottles, plastic bag, multi-dish, multi-tray, multi-plate, spiral film, glass beads, propagator, and the like. Microcarrier culture methods, such as polymer beads or glass beads, can also be used. Microcarrier can be made of dextran, polyocrylamide, polystyrene cellulose, gelatin, and glass. The microcarriers may optionally be coated with collagen, or negative charge of dimethylanimoethyl, diethylaninopropryl, and trimethyl-z-hydroxyamion propryl groups.

Following colony formation on the substrate, the colonies may be optionally purified by methods including concentration of suspended particles, extraction, adsorption ion exchange, and the like.

The resultant pure cultures of the *Vibrio* species are then placed into a medium used as a seed culture in subsequent steps. Transfer may occur by fitting a hose and tank coupling device to the bioreactor. In another embodiment, the culture may be transferred first to a sterile metal container which is attached to the seed fermenter. The medium in the seed culture may consist of amounts of sugars, carbon, nitrogen, water, minerals, salts, polyols, and other elements required for growth. Natural ingredients, such as soy peptones, oatmeal, and the like can also be used. In one embodiment, the medium is comprised of a soy peptone in an amount of from about 0.25 g to about 1 g, yeast extract in an amount of from about 0.25 g to about 1 g, glucose in an amount of from about 0.25 to about 1 g, distilled water, an agent for pH adjustment, at a pH of between 7.0 to 7.7. Incubation of the seed culture may occur between 20-30° C. for 24 to 48 hours, the seed medium may be from 150 mL to 1000 mL in volume.

The number of successive steps involving growth in the seed medium can depend on the scale of the production of TTX in the final phase. From stage to stage, there can be a tenfold volume increase in inoculum volume. However, in some embodiment, the inoculum volume can be larger than a tenth of the fermenter volume.

The culture may then be transferred to the fermenter. In one embodiment, transfer is accomplished by air pressure. The medium in the fermenter can be comprised of soy protein, yeast extract, sugars, distilled water, and the like. In one embodiment, soy protein is used in an amount from about 0.25 g to about 1.0 g, yeast extract is an amount from about 0.25 g to 1.0 g, sucrose from about 2.5 g to about 10 g, distilled water to level, and a buffer to adjust pH to about 7.1 to about 7.7, for example 2M ammonia or 2M hydrochloric acid. The fermenter chamber has a temperature between 28° C. to 35° C., and the medium is supplied with sterile air and agitation.

To the fermenter medium, a growth tissue extract is added simultaneously with the culture. Simultaneously does not refer to both the culture and the growth tissue extract being added at the same precise moment, rather it refers to the culture and the growth tissue extract being in the fermenter, specifically the fermenter medium, at the same time. The growth tissue extract or the culture may be added one before the other and vice versa. The growth tissue extract and the culture may inoculate in the medium for the same period of time, or one slightly less time than the other. Modifications in the length of times of either remaining with the medium is within the scope of this invention and is not a derivation therefrom. As will be discussed later, the growth tissue extract is called such because of its possession of growth factor elements.

The growth tissue extract can be taken from the organism used in obtaining the culture 101. In another embodiment, the growth tissue extract may be taken from a different organism or species provided such organism provides growth factors and TTX synthesis is exhibited in its tissue. The growth tissue extract may be obtained from the skin, intestine, liver, or ovary of the organism. In one embodiment, the extract is obtained from the liver or ovary. Following excising of the growth tissue extract, the extract is homogenized with a saline solution, and sterilized by filtration. The extract, prior to use, may be stored at between about −80° C. to about −60° C. The extract can be inoculated with the fermenter medium at a concentration of between about 0.5 g/L to about 1.5 g/L.

Through the addition of the extract to the fermentation medium with the culture, it is believed growth of TTX will be synergistic as compared with the culture in the medium by itself. Such synergistic growth is likely brought about through growth factors added via the tissue extract.

Fermentation is allowed to continue for at least 60 hours, or until there is an initial drop in observed cell density due to cell lysis. In isolating tetrodotoxin 105 from the fermenter medium, as will be discussed later, various steps may be used in conjunction, for example centrifuging, filtration, solvent extraction, ion exchange, adsorption, elution, pH-adjustment, heating, evaporation, drying, and other steps as deemed necessary to obtain highly pure, high yield tetrodotoxin (TTX). In one embodiment, a yield of at least 90% pure TTX is obtained in an amount of at least 0.5 mg TTX/L in a maximum of 3 to 5 days. In another embodiment, a yield of over 95% pure TTX in an amount of 1 mg TTX/L in a maximum of 5 to 7 days is obtained.

FIG. 2 is an embodiment of the method of isolating and purifying TTX from the culture in accordance with the instant invention.

In the method, the fermentation medium is firstly pH adjusted 201 to between 3.0 and about 4.0. In one embodiment, this is done with an acid such as hydrochloric acid. Additionally, the medium is heated to between 90° C. and 100° C. for approximately 8 to 12 minutes. The medium is then centrifuged 203, such as by a tubular-bank centrifuge, disk centrifuge, filtering centrifuge, vertical basket centrifuge, and the like. The medium may be centrifuged at a speed of 2000 to 9000 rpm for a period of between 10 minutes to 20 minutes at a temperature of 1° C. to 10° C. The supernatant liquid is then retained 205 and pH-adjusted to around 6.

Next, the supernatant liquid is evaporated 207. Evaporation may occur through an evaporation system that consists of one or more evaporators, installed in series. The evaporators may be selected from forced circulation, submerged-tube forced circulation, oslo-type circulation, short-type vertical, propeller calandria, long-tube vertical, reairculating longtube vertical, falling film, horizontal tube, and the like. The supernatant can be evaporated at a temperature between about 40° C. and 55° C., preferably at a reduced pressure. The supernatant is evaporated to between 2% to about 8% of its original volume, resulting in the resultant TTX.

An adsorption medium, such as activated carbon, is then mixed with the resultant TTX 209. The adsorption medium is preferably used in an equal volume to the resultant toxin extract.

An elution step on the adsorption medium is then performed 211. In a preferred embodiment, the adsorption medium is eluted at least 2 times, more preferably 3 times. The elution may occur through a 1:20 acetic acid/ethanol solution.

An evaporation of the eluant collected may be performed 213. In one embodiment, evaporation may occur between 40 to 50° C. in reduced pressure. Evaporation occurs until the eluant is between 0.5% to 2% of its original volume. In an alternate embodiment, prior to evaporation 213, the eluant may be pH-adjusted to around pH 6.

Following evaporating, the resultant extract, TTX, is loaded unto an ion exchange column 215. In a preferred embodiment, the column is packed with weak cation exchange resin beads. The toxic extract is then eluted therefrom 217, with a weak acid, for example 0.5% acetic acid. The extract can then be pH adjusted to around 6, and evaporated 219 between 40° C. to 50° C. under reduced pressure to about 0.5% to 2% of its original volume.

The extract can be dried 221, for example by freeze drying, spray drying, vacuum drying, fluid bed drying, etc., following by dissolution in water such as distilled water, ddw, and the like. The resultant solution is loaded unto another column 223, such column preferable possessing weak cation exchange resin beads. The column is eluted 225, and the eluant collected. The resultant eluant extract can be pH adjusted to around 6, followed by evaporation 227 between 40° C. to 50° C. to between 0.5% and 2% of its volume. The extract can then be dried, such as by freeze drying, spray drying, vacuum drying, fluid drying, etc.

As stated previously, the resultant TTX is at least 90% pure TTX, and in a preferred embodiment, over 95% pure TTX.

Adjustment to the above methods may be made to meet the needs of scale-up without deviating from the scope and breath of this application. Techniques in scaling up are well known in the art and to those skilled therein.

Example

Several strains of *Vibrio* species were screened and isolated from the intestines of puffer fish species *Takifugu alboplumbeus*. The strains was stored on ORI agar plates at 4 degrees Celsius and subcultured to fresh plates before inoculation to culture media.

All culture media were sterilized by autoclaving at 121 degree Celsius for 20 minutes. Seed medium was prepared from the following components (per 1000 ml of medium):

TABLE 1

| Phytone-peptone | 1.0 g |
|---|---|
| Yeast extract | 1.0 g |
| Glucose | 1.0 g |
| Distilled water | to 1000 ml |
| pH | 7.5 |

(adjusted with 1M NaOH)

A discrete colony of each *Vibrio* species on an agar plate was transferred aseptically with an inoculation loop and was suspended in 250 ml seed medium in a 500 ml culture flask. The inoculated culture was incubated at 25 degrees Celsius for 24-48 hours in an incubation shaker at 100 rpm.

*Takifugu alboplumbeus* tissue extract was prepared from the following components and sterilized by filtration through a 0.2 µm membrane:

TABLE 2

| Ovary (*Takifugu alboplumbeus*) | 100 g |
|---|---|
| Phosphate buffered saline | 100 ml |
| pH | 7.5 |

(adusted with 2M hydrochoric acid)

A fermentation medium was prepared from the following components (per 1 L of medium):

TABLE 3

| Phytone-peptone | 1.0 g |
|---|---|
| Yeast extract | 1.0 g |
| Sucrose | 10 g |
| Distilled water | to 1000 ml |
| pH | 7.5 |

(adjusted with 2M ammonia or 2M hydrochloric acid)

200 ml of seed culture and 10 g of *Takifugu alboplumbeus* tissue extract were used to inoculate 10 L fermentation medium aseptically in a 12 L fermenter. The fermenter was supplied with sterile air and agitation, and was maintained at a temperature of 30 degrees Celsius and a pH of 7.5 for 3 days.

The fermentation process was completed after at least 60 hours when initial drop in cell density due to cell lysis observed. Before collecting the fermentation medium from the fermenter chamber, the pH of the medium is adjusted to 3.5 with 2M hydrochloric acid and heated to 95° C. for 10 minutes. The medium is centrifuged at 8000 rpm at 4° C. for 15 minutes to remove microscopic cells. Only the supernatant in each centrifuge tube is retained, which is then adjusted to pH 6 with 2M ammonia solution. The pooled supernatant is evaporated at 45° C. under reduced pressure to 5% of its original volume and then mixed with an equal amount of activated carbon (v/w). The adsorbed toxin in the carbon is eluted with 1% acetic acid in 20% ethanol for three times. The eluant is adjusted to pH 6 with 2M ammonia before evaporation at 45° C. in reduced pressure to 1% of its original volume. The toxin extract is loaded onto a column (3×50 cm) of weak cation exchange resin (Bio-Rex® 70 Resin). The toxin is eluted with 0.5% acetic acid and the toxic fractions are monitored with HPLC analyses or mouse bioassay. The toxic factions are pooled together and adjusted to pH 6 with 2M ammonia solution before evaporation at 45° C. under reduced pressure to 1% of its original volume. The extract is freeze-dried and then dissolved in distilled water, which is loaded onto another column (1×80 cm) of weak cation exchange resin (Bio-Rex® 70 Resin). The toxin extract is eluted with 0-0.2% acetic acid (linear gradient) and the toxic fractions are monitored with HPLC analyses or mouse bioassay. The toxic factions are pooled together and adjusted to pH 6 with 2M ammonia solution before evaporation at 45° C. under reduced pressure to 1% of its original volume. The extract is finally freeze-dried and it gives over 95% pure TTX.

FIG. 3 compares the production of TTX in accordance with the present invention 301 against TTX production by prior methods 303, and TTX production by simply growing the *Vibrio* culture in a flask 305. As shown by FIG. 3, TTX production via the present invention 301 is quite rapid, yielding 0.5 mg TTX/L within 3 days. The prior art 303 shows 0.4 mg TTX/L within 6 days, and less than 1.1 mg TTX/L by mere flask culturing 305 in over 10 days.

The above system and measurement in accordance with the present invention can be controlled and monitored by instrumentation and control system. Such instrumentation and control system may contain on-line sensors, such as probes including thermometer, thermometer, pH reference electrodes, Ag and Pb probes, conductance probes, capacitance probes, on-line instruments including tachometers, watt-meters, mass flow meters, rotameters, strain gauges, load cells, spring diaphragm, oil filled diaphragm, electro magnetic flow meters, vortex devices, and gas analysers including paramagnetic analyser, mass spectrometers, and infrared analyser. Off line instruments can also be included, such instruments to measure packed cell volume, dry weight, optical density, microscopic observation, Coulter counter, and plate counts. The control systems may also comprise one or more controllers, such controller possessing processors, memory both temporary and permanent, algorithms for operating the production and fermenters, User Interface Devices, including displays, keyboard, mouses, etc. Examples of controllers include computers, pda's, laptop computers, and control panels.

Having described embodiments of the present system with reference to the accompanying drawings, it is to be understood that the present system is not limited to the precise embodiments, and that various changes and modifications may be effected therein by one having ordinary skill in the art without departing from the scope or spirit as defined in the appended claims.

In interpreting the appended claims, it should be understood that:

a) the word "comprising" does not exclude the presence of other elements or acts than those listed in the given claim;

b) the word "a" or "an" preceding an element does not exclude the presence of a plurality of such elements;

c) any reference signs in the claims do not limit their scope;

d) any of the disclosed devices or portions thereof may be combined together or separated into further portions unless specifically stated otherwise; and e) no specific sequence of acts or steps is intended to be required unless specifically indicated.

The invention claimed is:

1. A method of biosynthesizing tetrodotoxin, comprising:
   inoculating a culture medium providing a pure culture of *Vibrio alginolyticus*;
   excising a tissue from a tetrodotoxin-bearing organism, homogenizing the excised tissue, filtering to sterilize the homogenized tissue, thereby obtaining a tissue extract from the tetrodotoxin-bearing organism with said *Vibrio alginolyticus* pure culture and adding said tissue extract obtained from the tetrodotoxin-bearing organism to the inoculated culture medium;
   transferring said culture medium of *Vibrio alginolyticus* and tissue extract to a fermenter, wherein the inoculated culture medium is allowed to ferment under conditions suitable to produce tetrodotoxin, thereby biosynthesizing tetrodotoxin, wherein the culture medium in the fermenter is exposed to sterile air and agitation; and
   isolating and purifying the biosynthesized tetrodotoxin from the fermented culture medium,
   wherein the biosynthesized tetrodotoxin is at least 90% pure and is produced in an amount of about 0.5 mg/L of culture medium over a course of 3-5 days.

2. The method of in claim 1, wherein the tissue is excised from the ovary of the tetrodotoxin-bearing organism.

3. The method of claim 1, wherein the tetrodotoxin-bearing organism is a tetrodotoxin-bearing puffer fish.

4. The method of claim 3, wherein the puffer fish is *Takifugu alboplumbeus*.

5. The method of claim 1, wherein the fermenter is selected from the group consisting of a shake flask, aeration-agitation bioreactor, percolated impellor bioreactor, draught tube air-lift bioreactor, air-lift loop bioreactor, rotating drum bioreactor, and spin filter bioreactor.

6. The method of claim 1, wherein the culture medium is comprised of soy peptone, yeast extract, glucose, and distilled water.

7. The method of claim 1, wherein the tissue extract contains one or more growth factors.

8. The method of claim 1, wherein the isolation and purification of the biosynthesized tetrodotoxin comprises:
   adjusting pH of the fermented culture medium to between 3.0 and about 4.0;
   heating the fermented culture medium to a temperature between 90° C. to 100° C.;
   centrifuging the heated fermented culture medium to obtain a supernatant comprising the biosynthesized tetrodotoxin;
   evaporating said supernatant with an evaporation system that consists of one or more evaporators, installed in series, to obtain concentrated supernatant;
   mixing the concentrated supernatant with an adsorption medium;
   adding an acetic acid/ethanol solution to the concentrated supernatant and adsorption medium to obtain a first eluant;
   evaporating the ethanol from the first eluant to obtain a first sample of concentrated acetic acid and tetrodotoxin;
   loading the first sample onto a ion exchange column;
   adding a weak acid to said ion exchange column to obtain a second eluant;
   evaporating the weak acid from the second eluant to obtain a second sample of concentrated weak acid and tetrodotoxin; and
   freeze drying the second sample, thereby obtaining purified biosynthesized tetrodotoxin.

9. The method of claim 8, further comprising dissolving the freeze-dried tetrodotoxin sample in water, loading the dissolved sample onto a second ion exchange column having weak cation exchange resin beads, eluting the sample from the second column, and freeze-drying the sample, thereby obtaining purified biosynthesized tetrodotoxin.

10. The method of claim 1, wherein the purified biosynthesized tetrodotoxin is over 95% pure and is produced in an amount of 1 mg/L of culture medium over a course of 5-7 days.

11. A method of biosynthesizing tetrodotoxin, comprising:
   providing a pure culture of *Vibrio alginolyticus*;
   excising a tissue from a tetrodotoxin-bearing organism, homogenizing the excised tissue, filtering to sterilize the homogenized tissue, thereby obtaining a tissue extract from the tetrodotoxin-bearing organism;
   inoculating a culture medium with said *Vibrio alginolyticus* pure culture and adding said tissue extract obtained from the tetrodotoxin-bearing organism to said inoculated culture medium, and wherein the culture medium has a pH of about 7.1 to about 7.7 and consists essentially of soy protein, yeast extract, glucose, and water;
   transferring said culture medium of *Vibrio alginolyticus* and tissue extract to a fermenter, wherein the inoculated culture medium is allowed to ferment under conditions suitable to produce tetrodotoxin, and thereby biosynthesizing tetrodotoxin, wherein the culture medium in the fermenter is exposed to sterile air and agitation;
   adjusting the pH of said fermented culture medium to between 3.0 to about 4.0;
   heating the fermented culture medium to a temperature between 90° C. and 100° C.;

centrifuging the heated fermented culture medium to obtain supernatant comprising biosynthesized tetrodotoxin;

adjusting the pH of the supernatant to around 6.0; then evaporating said supernatant with an evaporation system that consists of one or more evaporators, installed in series, to obtain concentrated supernatant;

purifying the biosynthesized tetrodotoxin from the concentrated supernatant using a first ion exchange column and a second ion exchange column having weak cation exchange resin beads, wherein the biosynthesized tetrodotoxin is produced in an amount of at least 0.5 mg/L of culture medium over the course of 3 to 5 days, and wherein the purified biosynthesized tetrodotoxin is at least 90% pure and is produced in an amount of about 0.5 mg/L of culture medium over a course of 3-5 days.

12. The method of claim 11, wherein the biosynthesized tetrodotoxin is produced in an amount of 1 mg/L of culture medium over a course of 5 to 7 days, and wherein the purified biosynthesized tetrodotoxin is over 95% pure.

* * * * *